United States Patent [19]

Sills et al.

[11] Patent Number: 4,676,986

[45] Date of Patent: Jun. 30, 1987

[54] *SCHWANNIOMYCES CASTELLII* STRAINS AND BREWING PROCESS

[76] Inventors: Alexander M. Sills, 1200-875 Wonderland; Graham G. Stewart, 32 Stuyvesant Place, both of London, Ontario, Canada

[21] Appl. No.: 867,001

[22] Filed: May 20, 1986

Related U.S. Application Data

[63] Continuation of Ser. No. 493,526, May 11, 1983, abandoned.

[51] Int. Cl.[4] .......................... C12P 1/00; C12N 9/24; C12N 1/18
[52] U.S. Cl. ......................................... 426/29; 435/93; 435/200; 435/202; 435/203; 435/256; 435/911
[58] Field of Search .................... 426/29; 435/93, 200, 435/202, 203, 256, 911

[56] References Cited

U.S. PATENT DOCUMENTS

3,379,534  4/1968  Gablinger et al. .............. 99/31

OTHER PUBLICATIONS

Oteng-Gyang et al, Chemical Abstracts, 92(1980) #211578g.
Moresi et al, Enr. J. Appl. Microbiol. Biotech., 18(1983) 92-9.
Dhawale et al, Biotech. Lett. 5(1983) 185-90.
Dhawale et al, Biotech. Lett. 5(1983) 825-30.
Frelot et al, Biotech. Lett. 4(1982) 705-708.
Oteng-Gyang et al, Z. Allg. Mikrobiol. 21(1981) 537-44.
Clementi et al, Antonie van Leewenhoek, 46(1980) 399-405.
Willox et al, "The Addition of Starch Debranching Enzymes to Mashing and Fermentation", MBAA Technical Quarterly, vol. 14, No. 2, 1977; pp. 105-110.
"Which Light Process is Right?", Beverage World, Nov. 1978; pp. 154-161.
Oteng-Gyang et al, "A Study of the Amylolytic System of *Schwanniomyces castellii*", Zeitschrift fur Ailgemeine Mikrobiologie, vol. 21, No. 7, 1981, pp. 537-544.
Marschall et al, "Enzymes in Brewing", Brewers Digest, Sep. 1982, pp. 14-22.

*Primary Examiner*—Christine M. Nucker
*Attorney, Agent, or Firm*—Fisher, Christen & Sabol

[57] ABSTRACT

The present invention relates to amylolytic enzymes produced by strains of *Schwanniomyces castellii* which enzymes are relatively thermolabile under the conditions used to pasteurize beer. The present invention is also concerned with a novel strain of *Schwanniomyces castellii* which is a derepressed producer of alpha-amylase. Also disclosed is an improved process for the production of low carbohydrate beers and in particular, low calorie beers, from high gravity worts which improvements are facilitated through the use of culture filtrates derived from viable cultures of *Schwanniomyces castellii*.

20 Claims, 10 Drawing Figures

FIG. 1

*One unit is defined as the quantity of protein indicating $\Delta E^{1cm}_{500nm}$ of 0.1 using soluble starch and iodine.

*SCHWANNIOMYCES CASTELLII* STRAINS AND BREWING PROCESS

This application is a continuation of application Ser. No. 493,526, filed May 11, 1983, now abandoned.

FIELD OF THE INVENTION

The present invention relates generally to improvements in the brewing of beer and more particularly, to yeast strains of the species *Schwanniomyces castellii* and to thermo sensitive enzymes produced by those strains.

BACKGROUND OF THE INVENTION

Starch is the principal carbohydrate constituent of all brewers' grains including malt, unmalted barley and non-malted cereal adjuncts, including corn and rice. The starch, regardless of the source, is a high molecular weight polymer consisting of glucose units joined primarily by alpha-1,4 glucosidic bonds but also including a smaller number of alpha-1,6 glucosidic bonds. The former type of bond occurs in the linear chains of glucose units while the latter type result in inter-chain branch points that are characteristic of a particular sub-group of starch known as amylopectins. Most starches comprise about 25% amylose and about 75% amylopectin.

In the brewing process, starch is first broken down during the mashing stages by alpha and beta amylases. As a result of this enzymatic activity, a spectrum of non-fermentable soluble dextrins and fermentable sugars are formed. The majority of these dextrins are alpha-1,6 linked carbohydrates. The soluble starch hydrolysates are then extracted from the spent grains as a wort solution which can subsequently be fermented to produce beer. The fermentable carbohydrates such as glucose, maltose and maltotriose are fermented by the brewers' yeast to produce ethanol while the higher molecular weight dextrins, being non-fermentable, remain substantially unchanged in the final beer and contribute to its body and smoothness. The presence of these unfermentable, high molecular weight oligosaccharides is therefore acceptable, and even desirable, in the production of "regular" or conventional beers, despite the fact that they also contribute about four per cent, on a weight by volume basis, of carbohydrate. In the production of the so-called "light" beers, however, these non-fermentable or marginal dextrins represent a source of unwanted calories. A variety of processes exist, any one of which is at least nominally suitable for dealing with these non-fermentable carbohydrates in a manner which ultimately reduces the number of calories per unit volume in a fermented wort. One such process involves the breakdown of the carbohydrate into fermentable sugars through the enzymatic hydrolysis of the alpha-1,4 and alpha-1,6 glucosidic linkages. By means of such a process the non-fermentable carbohydrates may be effectively and economically utilized towards the production of ethanol.

One process relating to the production of low dextrin beers is disclosed in U.S. Pat. No. 3,379,534. That process is facilitated through the use of an amyloglucosidase(syn.,glucoamylase)-containing preparation which acts to hydrolyse the alpha-1,4 and alpha-1,6 linkages which are characteristic of the marginal dextrins. In accordance with the teachings of that patent, this enzymatic activity reduces the residual dextrin content which permits a reduction of the caloric content of the beer and also makes better use of the starch materials by converting a larger proportion thereof into fermentable sugars. The amyloglucosidase-containing preparation is obtained as a culture filtrate from a fungal species, *Aspergillus niger*. This species of fungus has long been recognized as the principal source of commercial amyloglucosidase enzymes.

Amyloglucosidase derived from this fungal source and, indeed from any other known sources of such enzymes, suffer from a disadvantage attributable to these enzymes intrinsic thermal stability. Amyloglucosidase derived from *Aspergillus niger* species are commonly employed in the commercial production of starch hydrolysates such as dextrose syrups wherein the reaction millieu is typically held at about 60° C. for periods of around seventy-two hours in duration. It will, of course, be appreciated that the rate of thermal denaturation of these enzymes in the pasteurization of beer is accelerated by the presence of ethanol in, and the acid pH of, the beer; however, that acceleration notwithstanding, it has been shown that such enzymes will not be adequately inactivated under the relatively mild pasteurization conditions to which beers are normally subjected. Thus, amyloglucosidases derived from *Aspergillus niger* culture filtrates and utilized in the hydrolysis of marginal dextrins in the brewing of beer must be employed prior to the kettle boiling of the wort, otherwise the enzymes survive in the finished, bottled product. The implications of that survival are three-fold: first, the enzyme will continue to act in the finished product on any remaining marginal dextrins to produce lower molecular weight fermentable carbohydrates such as glucose. Thus, at the very least, the beer will become a "sweet" beer. Secondly, if any viable yeasts or spores remain in the finished product, such organisms will act on the newly available fermentable carbohydrates and the finished product will undergo further fermentation. Either the sweetening of the beer and/or the fermentation of the newly formed carbohydrates will cause uncontrolled, and therefore undesirable, changes in the finished product after it has left the brewery. This aspect of the amyloglucosidase problem is briefly alluded to in an article appearing in the September, 1982 issue of "Brewers' Digest", beginning at page 14 thereof. This article, entitled "Enzymes in Brewing" by Marschall et al, suggests that the use of amyloglucosidase in the production of light beer, in view of the problems currently attendant such use will most likely depend upon the commercialization of immobilized enzyme technology whereby the amyloglucosidase enzymes will not be retained in the treated beer. Thirdly, brewing apparatus may become contaminated with the thermally stable enzyme which may result in "regular" beers becoming contaminated and detrimentally modified. The thermal stability of the enzyme may complicate its eradication from contaminated equipment. These problems are all addressed in an article by I. C. Wilcox et al, appearing in the MBAA Technical Quarterly, Vol. 14, No. 2, 1977 at page 105.

It is an object of the present invention to provide amylolytic enzymes derived from the yeast species *Schwanniomyces castellii* which enzymes are thermolabile under normal beer pasteurization conditions, relative to amylolytic enzymes derived from species of the genus *Aspergillus*.

SUMMARY OF THE INVENTION

Amylolytic enzymes, which term hereinafter includes only alpha-amylase and amyloglucosidase produced by *Schwanniomyces castellii*, have been found to be sensitive to beer pasteurization conditions. In accordance with one aspect of the present invention, therefore, there is provided a culture filtrate having thermo sensitive amylolytic enzyme activity which filtrate is derived from cultures of viable yeasts of the species *Schwanniomyces castellii*, when cultured on amylolytic enzyme-inducing nutrient media. Ancillary to the provision of said filtrate, the present invention also provides for the amylolytic enzymes alpha-amylase and amyloglucosidase, as can be derived from said culture filtrate and particularly, from concentrated forms thereof.

Most preferably, the above-mentioned culture filtrate is derived from strains of *Schwanniomyces castellii* which are derepressed amylolytic enzyme producing mutant strains which are produced by the following process:
 (a) exposing an amylolytic enzyme producing wild type strain of *Schwanniomyces castellii* to a mutagenic agent under mutagenic conditions;
 (b) aseptically inoculating a nutrient medium wherein starch is the sole available carbon source and which medium also includes a concentration of non-metabolite glucose analog sufficient to ensure the repression of amylolytic enzyme production in the wild type strain, with the exposed strain resulting from step (a);
 (c) incubating the thus inoculated medium for a period of time and under such conditions as are generally suitable for the growth of yeasts, until individual colonies of mutant strain develop; and,
 (d) selecting and propagating the mutant strains so produced.

In accordance with a more specific aspect of the present invention, there is provided a novel mutant strain of *Schwanniomyces castellii* having the ascession No. NCYC 1461 and which is further characterized as being a derepressed producer of thermolabile amylolytic enzymes.

The present invention also relates to brewing processes adapted for the production of pasteurized beers wherein worts are prepared in accordance with processes generally recognized in the art and wherein the improvement comprises the addition of amylolytic enzymes derived from *Schwanniomyces castellii* to the cooled wort subsequent to kettle boiling but prior to pasteurization. This process is particularly suited to the production of low carbohydrate beers and, more particularly, and again in accordance with known procedures, the process is readily adapted to the production of low calorie beers.

DETAILED DESCRIPTION OF THE PRESENT INVENTION

In the course of the following detailed description of the present invention, reference will be made to the appended drawings in which.

The present invention relates, in part, to culture filtrates having thermosensitive amylolytic enzyme activity which culture filtrates are derived from amylolytic enzyme producing yeasts of the species *Schwanniomyces castellii*, such as for example, strain ATCC 26077 and strain NCYC 1461. The culture filtrate may be obtained by propagating the selected *Schwanniomyces castellii* strain on any suitable amylolytic enzyme inducing medium. As in the production of any enzyme, the selection of media will influence the respective yields of each of the enzymes of interest. Perhaps more important, however, is the engineering of a production mash which does not include undesirable enzyme production. In the case of the present invention, it has been found that *Schwanniomyces castellii* strains produce a ferulate decarboxylase which acts on certain wort constituents in beer production to produce 4-vinyl guaiacol which gives the resulting beer a generally undesirable off-flavour. It has also been found, however, that this ferulate decarboxylase is an inducible enzyme which is produced only in response to the presence of certain substrates such as ferulic acid or cinamic acid, for example. Accordingly, where the end use of the cultured filtrate or enzyme mixture makes the presence of such a decarboxylase undesirable, the corresponding inducing substrates should be omitted from the production mash.

A peptone-yeast extract medium supplemented with maltose has been found to be an excellent enzyme-inducing medium. The maltose may be replaced with a less expensive corn syrup, known as high-maltose syrup, which comprises 40% to 50% maltose, 15% to 20% maltotriose, 10% to 15% glucose and about 25% dextrins. The substitution of high-maltose syrup reduces the cost of the nutrient medium but at the same time maintains satisfactory levels of enzyme production relative to those obtained with the use of maltose.

The substitution of corn steep liquor in peptone-yeast extract has not proven to be entirely satisfactory since the enzyme production levels fell markedly when the thus substituted medium was employed.

Casein or soya bean hydrolysates have been found to substantially increase the production of the enzymes.

The optimum concentrations of high-maltose syrup, corn steep liquor and soya bean or casein hydrolysates are, respectively, 1% weight by volume, 1% weight by volume, and 0.5% weight by volume. It is noted that neither high-maltose syrup nor corn steep liquor contain ferulate decarboxylase inducing substrates.

Figure 1:
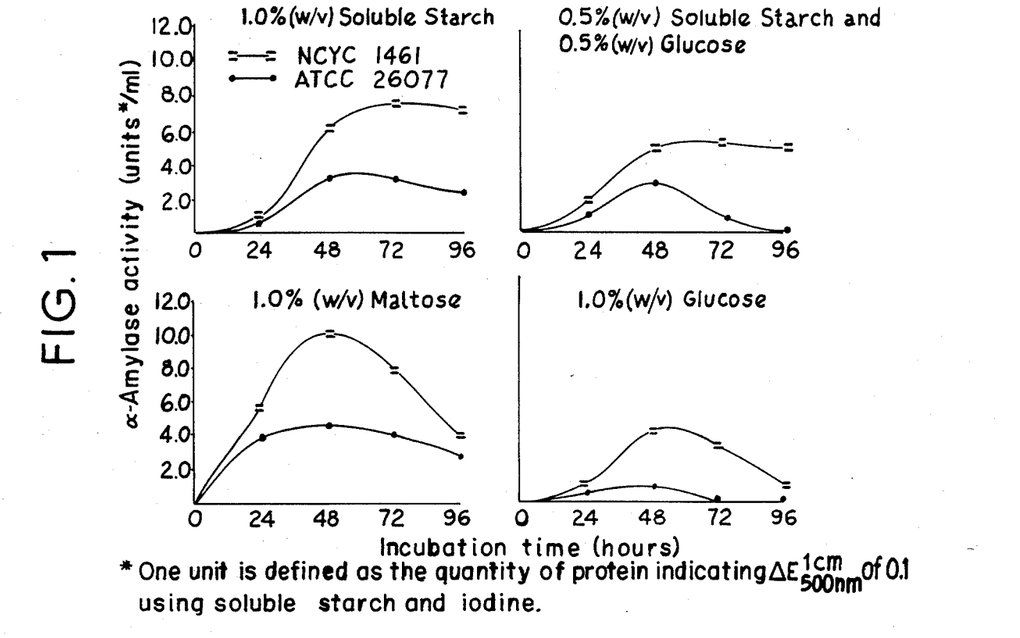
FIG. 1 illustrates the production of alpha-amylase by *Schwanniomyces castellii* strains utilizing various sources of carbohydrates as the principal carbon source in a nutrient media.
Figure 2:
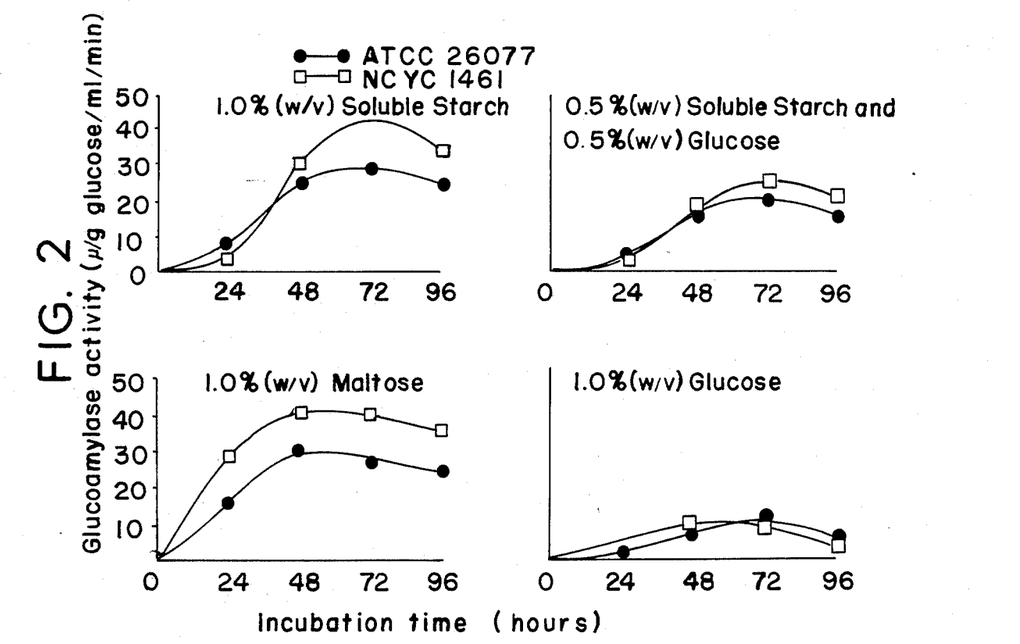
FIG. 2 depicts the production of amyloglucosidase by *Schwanniomyces castellii* strains on the nutrient media mentioned above in respect of FIG. 1.

In any case, following a suitable period of growth during which time the enzyme production is optimized, the culture medium is filtered to remove the microbial cells. The time required to achieve optimal enzyme production varies depending on the substrate being used. The effect of various substrates on the time required is illustrated in FIGS. 1 and 2 for alpha-amylase and amyloglucosidase, respectively. Generally, between forty-eight and seventy-two hours is preferred.

It will be remembered at this point that both the alpha-amylase and the amyloglucosidase enzymes that are produced by the *Schwanniomyces castellii* strains are extra-cellular enzymes and therefore cellular disruption is not necessary to enhance the enzyme yield. Furthermore, the filtrate does not exhibit any proteolytic activity (unlike filtrates derived from *Aspergillus* species) and the amyloglucosidase of the present invention has been discovered to have debranching activity unlike the amyloglucosidase produced by *Schwanniomyces diastaticus* strains.

Once the spent culture media has been filtered, the resultant clarified liquor may be concentrated, as for example by means of vacuum evaporators operated at suitably low temperatures and for a duration suitable to enhance the concentration of the crude enzyme solution. Generally, such concentration steps are limited by either the final vicosity of the resulting concentrate or by the precipitation of solids from the concentrate. Purer forms of the enzymes are then recoverable, for example, by means of either adsorbtion or precipitation techniques. While adsorbtion techniques, including the use of chromatographic columns, are often applied in the laboratory-scale recovery of enzymes, precipitation techniques are better adapted to the economics of commercial-scale recovery. Examples of applied commercial precipitation techniques are generally well known and include those utilized in the recovery of amylolytic enzymes from Bacillus subtilis filtrates obtained using submerged fermentation processes, or those employed in precipitating amylase enzymes obtained from the mould Aspergillus oryzae grown by way of semi-solid culture processes. The enzymes obtained from culture filtrates of the present invention may, if desired, be standardized on the basis of its rate of substrate activity. The general considerations applicable to the production of microbial enzymes are discussed in an article by E. J. Beckhorn, entitled "Production of Microbial Enzymes" which article appears on page 366 of *Microbial Technology* edited by H.J. Peppler and published by Reinhold Publishing Corporation.

In any case, the culture filtrate of the present invention is a source of relatively heat sensitive alpha-amylase and glucoamylase. Additonally, the amilyloglucosidase of the present invention is an alpha-1-6-debranching enzyme, as has already been indicated supra. The amylolytic system of *Schwanniomyces castellii* has been isolated and purified by means of ultrafiltration followed by polyacrylamide gel electrophoresis. There follows, immediately hereinbelow, a detailed description of one such isolation and purification of the above-mentioned amylolytic system which is intended to show, by way of example, one of the means by which the enzymes of the present invention can be obtained. An inoculum, consisting of *Schwanniomyces castellii* strain ATCC 26077 was introduced into 100 ml. aliquots of 2% weight by volume soluble starch containing the peptone-yeast extract nutrient medium of Ogur and St. John, which was prepared in accordance with the method disclosed in J. Bacteriol, 1956, 92, 500–504. The inoculated medium was incubated in 300 ml. flasks at 21° C. for forty-eight hours on a gyrorotary shaker at 160 rpm. Subsequently, the 100 ml. cultures were aseptically transferred to respective 2 liter flasks, each containing one additional liter of the nutrient medium mentioned above, and incubated under the same cultural conditions. After forty-eight hours of growth, the yeast cells were removed by centrifugation at 2000 gravities for 15 minutes and the resulting 1 liter supernatents were concentrated 200 to 250 fold by ultrafiltration at 2° C. under 60 psi pressure with a stirred ultrafiltration cell fitted with an ultrafilter having a 30,000 dalton cut off. The resulting 5 ml. crude preparation was further concentrated using a concentrator having a 15,000 dalton cut off, until the resulting preparation contained a protein concentration of 1.5 to 2 mg. per milliliter. Thirty-five microliter aliquots of the concentrated preparation were then loaded into respective sample wells containing 10% on a weight by volume basis of a polyacrylamide gel prepared as described by Shapiro et al in Biochem, Biophys, Res. Commun. 1967, 28, 815–820, with the exception that riboflavin replaced amoniumpersulphate and S.D.S. was omitted to prevent enzyme denaturation. A 50 milliamp electrophoretic current was applied across the gels and the electrophoresis was permitted to continue for approximately 16 hours. The gels were subsequently fractionated by cutting them into 5 millimeter slices which were then placed into individual test tubes containing distilled water. These tubes were then permitted to stand for forty-eight hours at 2° C. to allow for the elution of the enzymes from the gels. The resulting fractions were then assayed for alpha-amylase and amyloglucosidase activity. Alpha-amylase activity was measured by the iodine method described by Spencer-Martins and VanUden, European Journal of Applied Microbiology and Biotechnology, 1979, 6, 241–250. This assay was carried out using a 0.5% weight by volume soluble starch substrate in a 0.05 molar citrate-phosphate buffer at pH 5.5. One unit of alpha-amylase activity was defined as the quantity of protein required to produce a $\Delta E^{1\,cm} 550\,\mu m$, of 0.1 with a soluble starch/iodine system. The amyloglucosidase assay was carried out by measuring the glucose concentration released by the enzyme in a cell-free system, using 2% weight by volume dextrin as a substrate in a 0.1 molar citrate-phosphate buffer at pH 5.5.

Figure 3:
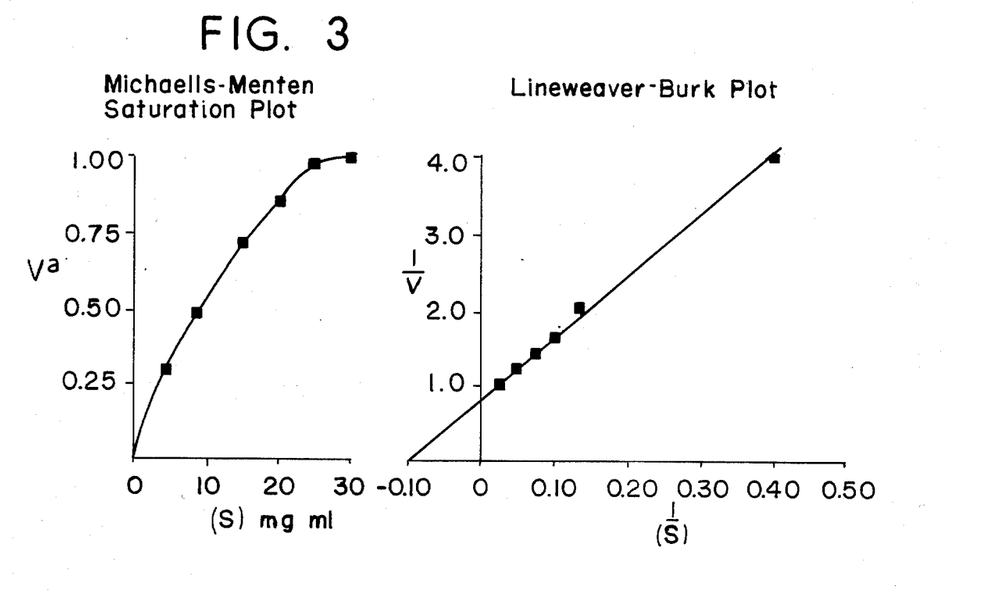
FIG. 3 are graphic representations of Michaelis-Menten saturation and Lineweaver-Burk enzyme kinetic plots pertaining to the activity of the alpha-amylase enzyme derived from *Schwanniomyces castellii;*

Referring now to FIG. 3 of the drawings, there is shown the characteristic kinetic perameters of the *Schwanniomyces castellii* alpha-amylase enzyme as represented by both Michaelis-Menten saturation and Lineweaver Burk enzyme kinetic plots. The $K_m$ and the V-max values for the alpha-amylase are, respectively, 1.15 mg. per ml., and 36 units per minute per miligram protein.

Figure 4:
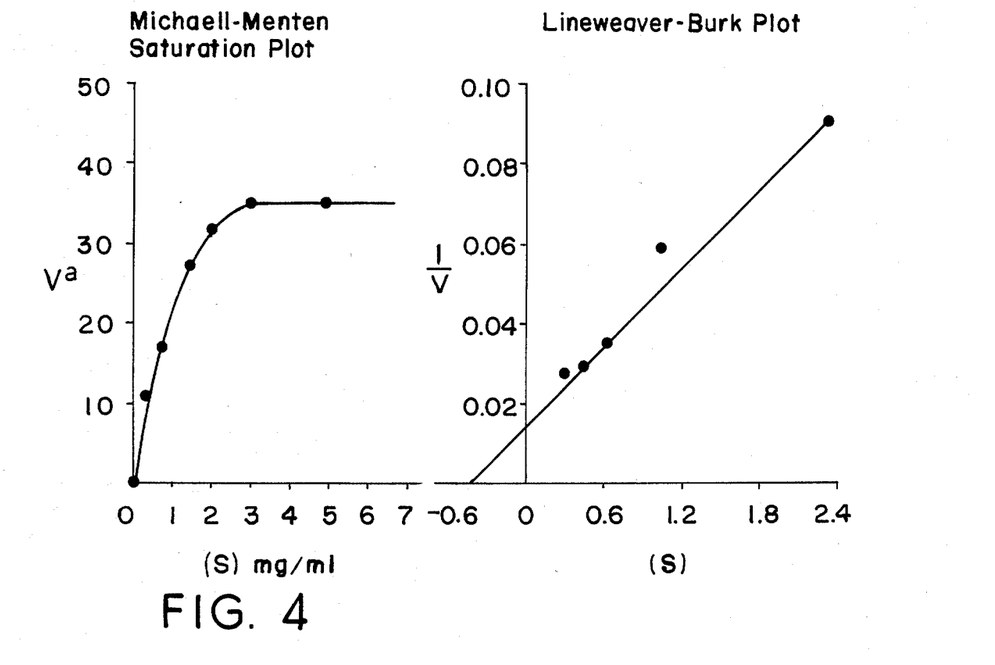
FIG. 4 depicts similar plots for the glucoamylase enzyme derived from *Schwanniomyces castellii;*

Referring now to FIG. 4 of the drawings there is shown similar plots for the amyloglucosidase enzyme obtained from *Schwanniomyces castellii*. The $K_m$ and V-max values for this amyloglucosidase enzyme are, respectively, 10.31 mg. per ml., and 1.19 millimoles of glucose per minute per miligram protein.

Purified samples of the respective alpha-amylase and amyloglucosidase enzymes were tested for carbohydrates. No carbohydrates were detected in association with the amyloglucosidase enzyme, however, in the alpha-amylase enzyme, carbohydrates were found to constitute 56% weight by weight of the total weight of the enzyme. The carbohydrate moeity of the alpha-amylase was found to be mainly glucosidic in nature.

Figure 5A:
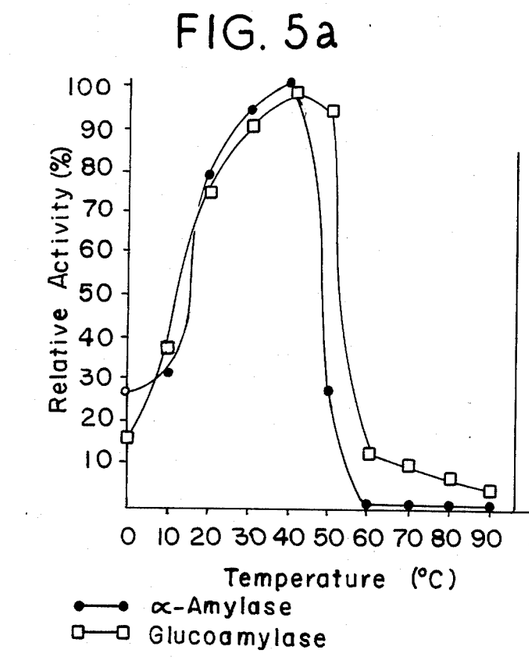
FIG. 5a depicts a graphical representation of the optimal temperatures for both the alpha-amylase and the glucoamylase enzymes derived from *Schwanniomyces castellii;*

Referring now to FIG. 5a of the drawings, there is shown a graphical representation of the optimal temperatures for alpha-amylase and amyloglucosidase respectively. In regard to the alpha-amylase enzyme derived from *Schwanniomyces castellii,* the optimum temperatures ranged between 30° C. and 40° C. Notably, approximately 75% of that activity was extant at 20° C. and there was a very rapid decline in activity at temperatures of 50° C. or higher. The amyloglucosidase enzyme exhibited a somewhat higher optimal temperature within the range of between 40° C. and 50° C. Again, it is noted that more than 75% of that activity was extant between 20° C. and 30° C. It will be appreciated, of course, that these relatively high levels of activity for both of these enzymes at temperatures ranging between 20° C. and 30° C. are of particular significance to enzymatic processes carried out at those temperatures, ie. brewing processes.

Figure 5B:
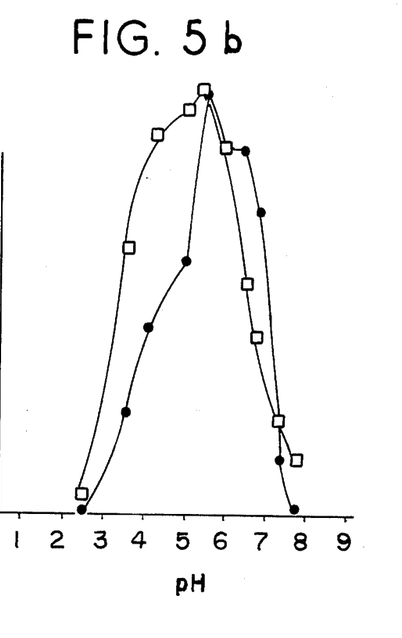
FIG. 5b depicts a graphical representation of these same enzymes' respective activities over a range of pH's.

Referring now to FIG. 5b of the drawings, there is shown a graphical representation which depicts the enzyme activity profile over a range of pH's. As shown in the graph, the optimal pH for the alpha-amylase activity was between pH 5.5 and 6.5, however, the amyloglucosidase activity gave an optimal pH at a slightly more acidic range of between 4.2 to 5.5.

Figure 6A:
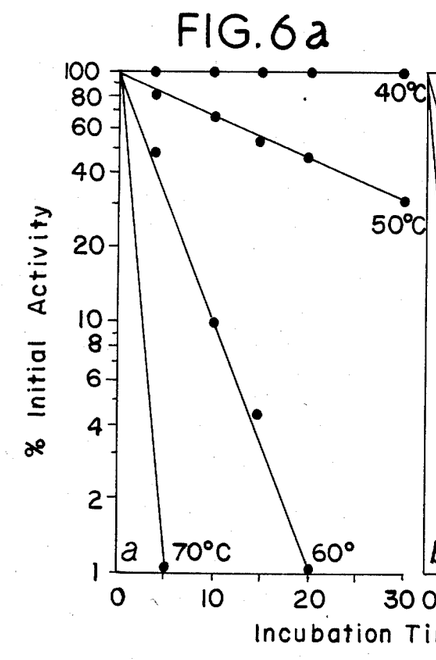
FIG. 6a is a graphical representation depicting the rates of thermo inactivation for various temperatures of the alpha-amylase enzyme derived from *Schwanniomyces castelli;*

Referring now to FIG. 6a, there is shown a graphic representation of the rates of thermal inactivation for various temperatures of the alpha-amylase enzyme derived from *Schwanniomyces castellii.* Incubation of the alpha-amylase enzyme at 60° C. and 70° C. after 20 and 5 minutes respectively resulted in a complete inactivation. Incubation at 50° C. resulted in a significant reduction in activity, 32% after 30 minutes, however, incubation at 40° C. had no effect on the activity of this enzyme.

Figure 6B:
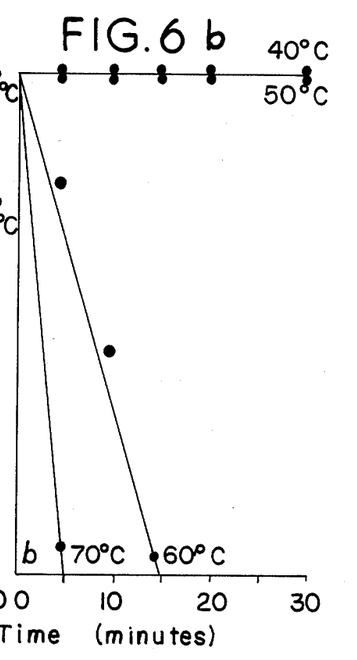
FIG. 6b depicts a graphical representation of the thermo inactivation rate of the glucoamylase enzyme derived from *Schwanniomyces castellii*, over a similar temperature condition.

Referring now to FIG. 6b, there is depicted a graphical representation of the thermal inactivation rate at various temperatures of the amyloglucosidase enzyme derived from *Schwanniomyces castellii.* The amyloglucosidase enzyme showed a higher temperature tolerance than the alpha-amylase enzyme mentioned above. Incubation of the amyloglucosidase enzyme at 50° C. for 30 minutes did not show any decrease in its activity. At 60° C. the amyloglucosidase was inactivated in 15 minutes and at 70° C., in 5 minutes. It will be appreciated, of course, in respect of both FIGS. 6a and 6b that the enhanced rates of thermal inactivation that result from the low pH and the ethanol concentration encountered in beers is not illustrated on these respective graphs. As stated above, both of these enzymes undergo complete thermal inactivation in beer products under normal brewing pasteurization conditions.

The relative hydrolytic rates of the alpha-amylase of the present invention were measured for various carbohydrates as are reproduced below in Table I for comparison purposes.

TABLE I

PERCENT HYDROLYSIS OF SEVERAL CARBO-
HYDRATES BY THE ACTION OF ALPHA-AMYLASE
ISOLATED FROM *SCHWANNIOMYCES CASTELLII*

| Substrate | Percent Hydrolysis$_{(a)}$ |
| --- | --- |
| Maltose | 4.1 |
| Isomaltose | 0.2 |
| Pullulan | 0.0 |
| Corn Starch | 62.6 |
| Potato Starch | 91.8 |
| Wheat Starch | 99.5 |
| Soluble Starch | 94.1 |
| Dextrin | 95.5 |

$_{(a)}$Percent hydrolysis determined with 1% (w/v) substrate using 0.1 mg protein/ml for 15 min. at 40° C.

As shown above, the percent hydrolysis of maltose, isomaltose and pullulan were compared on the basis of the concentration of glucose released and the percent hydrolysis of the different starches were determined by the reduction of the blue colour obtained with iodine. During the 15 minute incubation period, this alpha-amylase was able to hydrolyse most of the starches almost entirely with the notable exception of corn starch. On the other hand, maltose was found to be a very poor substrate and isomaltose and pullulan were not hydrolyzed at all.

A similar study of carbohydrate hydrolysis was undertaken for the amyloglucosidase enzyme of the present invention and the results appear below in Table II.

TABLE II

HYDROLYSIS OF SEVERAL CARBOHYDRATES
BY THE ACTION OF AMYLOGLUCOSIDASE
ISOLATED FROM *SCHWANNIOMYCES CASTELLI*

| Substrate | Amyloglucosidase Activity$_{(a)}$ |
| --- | --- |
| Maltose | 4.10 |
| Isomaltose | 3.86 |
| Pullulan | 0.53 |
| Corn Starch | 3.25 |
| Potato Starch | 3.16 |
| Wheat Starch | 3.25 |
| Soluble Starch | 3.31 |
| Dextrin | 2.45 |

$_{(a)}$mg glucose released/ml/hour

As indicated above, maltose was a very good substrate for this enzyme and isomaltose was hydrolyzed almost to the same extent indicating that the enzyme possessed the ability to cleave alpha 1,4 as well as alpha-1,6 glucosidic linkages. This debranching activity was confirmed by the ability of the enzyme to hydrolyze pullulan which is a long chain polymer consisting of maltotriosyl units joined by alpha-1,6 glucosidic linkages. The various starches were not utilized as readily as were the maltose or isomaltose substrates and the amyloglucosidase activity against the dextrins was considerably slower than against the larger molecular weight starches.

The present invention also relates to the production of a novel strain of *Schwanniomyces castellii.* The mutant strain *Schwanniomyces castellii* NCYC 1461 was produced by treating a known strain, *Schwanniomyces castellii* ATTC 26077 with known mutagenic agents. The survivors were cultured on potato starch agar in the presence of concentrations of deoxyglucose at least as high as $10^{-3}$ molar. Viable colonies produced on this medium were sampled and were found to be derepressed, mutant producers of the alpha-amylase enzyme. Accordingly, the selection of the mutant strain is particularly desirable in the production of the above-mentioned culture filtrate having amylolytic enzyme activity. By means of such a selection there is a large proportionate increase in the relative amount of alpha-amylase present in the clarified culture filtrate. This novel strain of *Schwanniomyces castellii* is available upon request from the Yeast Collection of the National Collection of Yeast Cultures Depository ("NCYC"), Food Research Institute, Norwich, Norfolk, England. The ascession number of that organism in the above-mentioned repository is NCYC 1461. *Schwanniomyces castellii* strain NCYC 1461 is one of a number of mutant strains of *Schwanniomyces castellii* that were produced by way of the above-outlined mutagenic treatment of *Schwanniomyces castellii* strain ATCC 26077. The particulars of the mutagenic treatments are detailed below in Table III which indicates the time of exposure, the percent survival rate, and the frequency of mutation for both of the treatments employed.

TABLE III

PRODUCTION OF *SCHWANNIOMYCES CASTELLII* MUTANTS RESISTANT TO 2-DEOXY-GLUCOSE ON POTATO STARCH AGAR USING EMS AND UV LIGHT AS MUTAGENIC AGENTS

A. EMS Treatment

| Time of Exposure (min) | % Survival | Frequency of Mutation |
|---|---|---|
| 0 | 100 | 0 |
| 30 | 66 | $10^{-3}$ |
| 60 | 14 | $2 \times 10^{-4}$ |

B. UV Treatment

| Time of Exposure (sec) | % Survival | Frequency of Mutation |
|---|---|---|
| 0 | 100 | 0 |
| 30 | 82 | $8 \times 10^{-3}$ |
| 60 | 27 | $1.8 \times 10^{-1}$ |

All of the surviving mutants were shown to have higher levels of alpha-amylase production than the wild type strain, ATCC 26077. The relative improvement of each of selected ones of these mutants is indicated below in Table IV.

TABLE IV

PRODUCTION OF ALPHA-AMYLASE BY THE WILD TYPE *SCHWANNIOMYCES CASTELLII* (STRAIN ATCC 26077) AND STRAINS RESISTANT TO 2-DEOXY-GLUCOSE

| | alpha-amylase activity (units[a]/ml) | |
|---|---|---|
| Strain | 48 hours | 72 hours |
| ATCC 26077 | 4.2 | 6.2 |
| UV 11 | 4.9 (20%[b]) | 10.1 (60%) |
| UV 18 | 8.7 (110%) | 15.3 (150%) |
| UV 30 | 5.1 (20%) | 10.8 (70%) |
| UV 31 | 7.4 (80%) | 12.5 (100%) |
| NCYC 1461 | 6.2 (50%) | 21.9 (250%) |
| EMS 7 | 4.4 (10%) | 13.9 (120%) |

[a]One unit defined as the quantity of protein mediating a $\Delta E_{550}^{lcm}$ $\mu m$ of 0.1 using soluble starch and iodine
[b]Percentage increase of alpha-amylase activity over the activity obtained in the ATCC 26077 strain.

The present invention also relates to an improved brewing process wherein amylolytic enzymes derived from strains of *Schwanniomyces castellii* are added to the wort once it has cooled subsequent to kettle boiling. These enzymes may act throughout the fermentation of the wort but, by their very nature, are destroyed or inactivated during the pasteurization of the beer. By this means, both the above-mentioned alpha-amylase enzyme and the amyloglucosidase enzyme are available throughout a prolonged period of time during which they act on the full range of dextrin material present in the wort. This, of course, has the incidental advantage of not requiring as high an enzyme concentration as would be required for an enzyme of similar activity when used in the relatively shorter mashing process. Furthermore, because the *Schwanniomyces castellii* amylolytic enzymes are sensitive to the pasteurization process, they do not survive in the packaged product, a result which is achieved in the absence of commercialized, immobilized enzyme technology. Moreover, the optimum temperature for the combined alpha-amylase and amyloglucosidase enzymes produced by *Schwanniomyces castellii* strains was about 40° C., a temperature more compatible with those encountered during the fermentation process than that of a similar combined enzyme system derived from *Aspergillus* species for which the optimum temperature is usually higher. The use of these *Schwanniomyces castellii* enzymes, whether as a culture filtrate or alternatively in more concentrated forms, is particularly suited to the production of low carbohydrate beers. Suitable modifications of such process, such as dilution, for example, can be utilized to produce low-calorie beers.

The enzymes of the present invention are most preferably added to the cooled wort at about the same time that the readily-fermentable carbohydrate sources, originally present in the wort, are exhausted in the course of fermentation. It was found, in this regard, that for a given quantity of those enzymes (or culture filtrate having a specified enzymatic activity) the degree or apparent attenuation of the final product was enhanced by delaying the addition of the enzymes until about forty to fifty hours of fermentation had passed. Thus, when the enzymes were added at the beginning of the fermentation, the increase in the degree of apparent attenuation as compared against a control brew to which no enzyme had been added, was about 5.0%. By delaying the addition of the same quantity of enzyme to about twenty hours after fermentation had begun, the degree of apparent attenuation was about 6.0% higher than that observed for the control brew. By delaying the time of addition by a further twenty hours, ie. until forty hours of fermentation had passed, the degree of apparent attenuation of the product was increased 8.4% over the above-mentioned control brew. The actual time of addition will, of course, depend on the particulars of the recipe being used and the characteristics of the yeast in question. A good estimator of the preferred time for addition of these enzymes, however, is, as indicated above, the concentration of the readily-fermentable carbohydrate present in the wort. Thus, it is preferred that these enzymes be added only after the concentration of such readily-fermentable carbohydrates have been substantially depleted by the yeasts present in the fermenting wort.

As concerns the amount of enzyme to be added in any given instance, this will also depend on the particulars of the recipe and the yeast being utilized, and accordingly, that amount is best determined by way of routine experiment. It will be appreciated, however, that there exists a direct co-relation between the amounts of the enzymes added and the resulting degree of apparent attenuation. More specifically, the larger the amount of enzyme that is added, the greater the degree of apparent attenuation that results. It will also be noted that when 80% of the amount of enzyme required to produce an apparent attenuation of 100% is added to the wort, the resultant degree of apparent attenuation is as high as 99.4%. Accordingly, an amount of enzyme ranging between about 60% and 80% of the amount required to produce a 100% apparent attenuation in the wort is preferred. The addition of an excess of the enzymes of the present invention to an experiment of brew has been found to result in the production of almost 20% more ethanol in that brew as compared with a control brew. Both of the brews in question were fermented with a production lager strain of Saccharomyces uvarrum (carlsbergensis).

EXAMPLE 1

Four liters of brewers' wort were prepared using conventional brewing techniques such that 70% of the extract in the wort was derived from brewers' malt and 30% derived from corn grits. This wort had an original gravity of 14.4° Plato. The wort was added into 4 fleakers containing one liter each and pitched with 0.3 g. of pressed yeast of a production lager strain of Saccaromyces uvarrum (carlsbergensis). Fermentation was allowed to proceed at a controlled temperature of 70° C. under anaerobic conditions and with mechanical stirring (required due to the small volume of fermentation). After 44 hours of fermentation, 20 mg. of enzymes prepared from Schwanniomyces castellii as indicated previously were added to 2 fleakers and the fermentation proceeded for a total of 168 hours.

Samples were taken during the fermentation and the ethanol concentration and wort attenuation were determined for each sample (see Table V below).

TABLE V

| Time (Hours) | Ethanol % (w/v) Control | Ethanol % (w/v) Enzyme Added | °Plato Control | °Plato Enzyme Added |
|---|---|---|---|---|
| 0 | 0 | 0 | 14.4 | 14.4 |
| 24 | 1.48 | 1.53 | 11.4 | 11.3 |
| 48 | 4.93 | 4.96 | 5.2 | 4.8 |
| 53 | 4.93 | 4.96 | 4.0 | 2.8 |
| 72 | 4.98 | 4.98 | 3.8 | 2.3 |
| 96 | 5.00 | 5.25 | 2.5 | 1.6 |
| 120 | 5.10 | 5.42 | 2.5 | 1.1 |
| 144 | 5.15 | 5.74 | 2.4 | 0.9 |
| 168 | 5.32 | 6.06 | 2.1 | 0.7 |

V

Figure 7:
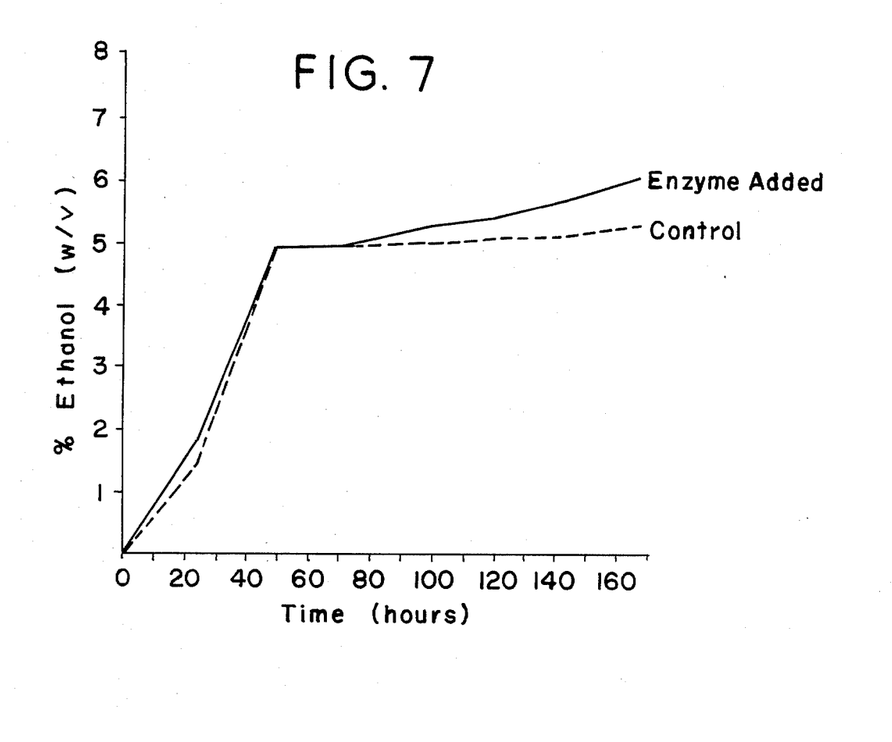
FIG. 7 depicts the evolution of ethanol on a percent weight by volume basis over time, based on the progress of the fermentation described in Example 1.
Figure 8:
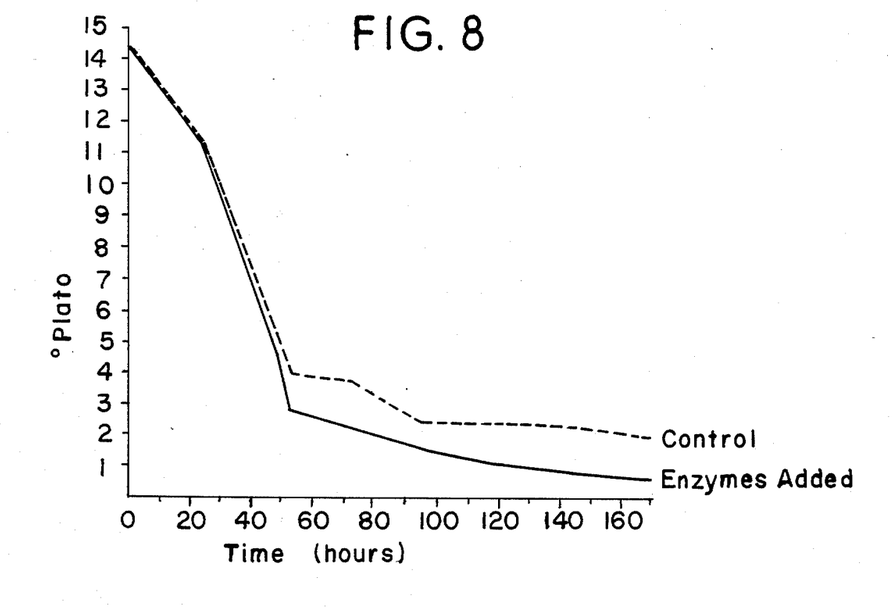
FIG. 8 depicts the reduction in the degrees Plato of the fermenting wort, also as per Example 1, over time.

The data presented in Table V above is also depicted, graphically, in FIGS. 7 and 8 of the appended drawings.

At the end of the fermentation, the beer was centrifuged, bottled and some samples were pasteurized. It was determined that in the non-pasteurized samples, both alpha-amylase and glucoamylase activity could be detected, however, no trace of activity could be detected in the pasteurized beer.

We claim:

1. A culture filtrate having thermo-sensitive amylolytic enzyme activity derived from cultures of viable Schwanniomyces castellii strain NCYC 1461 when cultured on amylolytic enzyme inducing nutrient media.

2. Amylolytic enzymes derived from a concentrated culture filtrate of claim 1.

3. Commercial enzyme preparations having thermolabile alpha-amylase activity and being derived from the culture filtrate of claim 1.

4. Commercial enzyme preparations having thermolabile amyloglucosidase activity and being derived from the culture filtrate of claim 1.

5. The culture filtrate of claim 1 wherein said nutrient medium does not contain ferulate decarboxylase inducing substrate.

6. The culture filtrate of claim 5 wherein said nutrient medium contains high maltose syrups as the principal carbon source.

7. A mutant strain of Schwanniomyces castellii having the ascession number NCYC 1461 and being further characterized as being capable of producing thermolabile amylolytic enzymes in the presence of concentrations of about $10^{-3}$ M deoxy-glucose.

8. A brewing process for producing pasteurized beers wherein the improvement comprises the addition of thermolabile amylolytic enzymes derived from Schwanniomyces castellii strain ATCC 26077 or strains produced therefrom, to the cooled wort subsequent to kettle boiling but prior to pasteurization of the beer.

9. The process of claim 8 wherein said brewing process is adapted for the production of low carbohydrate beers.

10. The process of claim 9 wherein said enzymes are added thirty to fifty hours after fermentation of the wort is initiated.

11. The process of claim 9 wherein the amount of enzymes added is between about sixty and eighty per cent of the amount of enzymes necessary to achieve one hundred per cent apparent attenuation of the wort.

12. The process of claim 9 wherein said enzymes are derived from derepressed amylolytic enzyme producing mutant strains of Schwanniomyces castellii, said strains having been produced by the process comprising the steps of:
(a) exposing an amylolytic enzyme producing wild type strain to a mutagenic agent under mutagenic conditions;
(b) aseptically innoculating a nutrient medium wherein starch is the sole available carbon source and which medium also includes a concentration of a non-metabolite glucose analogue sufficient to ensure the repression of amylolytic enzyme production in the wild type strain, with the exposed strain resulting from step (a);
(c) incubating the thus innoculated medium for a period of time and under such conditions as are generally suitable for the growth of yeasts until individual colonies of mutant strains develop; and
(d) selecting and propagating the mutant strains so produced.

13. The process of claim 12 wherein said mutagenic agent is ethyl-methane sulfonate.

14. The process of claim 13 wherein said wild type strain is exposed to said ethyl-methane sulfonate for between about thirty to sixty minutes.

15. The process of claim 12 wherein said mutagenic agent is ultra-violet light.

16. The process of claim 12 wherein said glucose analogue is deoxyglucose.

17. The process of claim 16 wherein said concentration is about $10^{-3}$ molar.

18. The process of claim 12 wherein said mutant strain is Schwanniomyces castellii strain NCYC 1461.

19. The process of claim 9 wherein said brewing process is adapted for the production of low calorie beers.

20. The process of claim 8 wherein said amylolytic enzymes are not contaminated with ferulate decarboxylase.

* * * * *